United States Patent
Dever et al.

(12) 
(10) Patent No.: US 6,303,140 B1
(45) Date of Patent: Oct. 16, 2001

(54) MEDICATED DEVICE FOR WARTS, CORNS, CALLUSES AND NAILS

(75) Inventors: Gerald R. Dever, Cordova; William Rogers, Memphis, both of TN (US)

(73) Assignee: Schering-Plough Healthcare Products, Inc., Memphis, TN (US)

( * ) Notice: Subject to any disclaimer, the term of this patent is extended or adjusted under 35 U.S.C. 154(b) by 0 days.

(21) Appl. No.: 09/417,943

(22) Filed: Oct. 13, 1999

(51) Int. Cl.$^7$ ............... A61F 13/00; A61K 9/70; A61K 7/04; A61K 9/00; A61K 9/14
(52) U.S. Cl. ............... 424/443; 424/61; 424/400; 424/449; 424/486
(58) Field of Search ............... 424/443, 400, 424/61, 449, 486

(56) References Cited

U.S. PATENT DOCUMENTS

| | | | | |
|---|---|---|---|---|
| 5,783,640 | * | 7/1998 | Sandstrom et al. | 525/329.3 |
| 5,886,074 | * | 3/1999 | Sandstrom et al. | 524/291 |
| 6,025,032 | * | 7/1998 | Gaveske | 427/393.6 |

* cited by examiner

*Primary Examiner*—Thurman K. Page
*Assistant Examiner*—S. Howard
(74) *Attorney, Agent, or Firm*—Robert J. Lipka

(57) ABSTRACT

A plaster preparation comprising a synthetic rubber; a reinforcing agent based on silica or random styrene-butadiene, copolymer; a tackifier; salicylic acid or a pharmaceutically acceptable salt or ester thereof.

21 Claims, No Drawings

MEDICATED DEVICE FOR WARTS, CORNS, CALLUSES AND NAILS

BACKGROUND

Self-adhesive topical products based on salicylic acid containing plasters as the active ingredient are used widely in a number of corn removers, callus remover and wart remover medicated patches sold over-the-counter (OTC). Many of these products are commonly based on natural rubber. However, many individuals are allergic to natural rubbers and government regulatory agencies have responded by mandating that medical devices containing natural rubber must bear label warnings of possible allergic sensitization after mid-1998. Another problem with presently available com/callus/wart remover plasters is that they are subject to a phenomena known as "cold flow" in which during storage the plaster or polymeric component tends to ooze out or extrude beyond the edge of the medicated disk. Further, a number of presently available plasters may not have adequate tack properties for adhering to the site of application on the skin. Thus, it would be desirable to provide a salicylic acid containing plaster for treating and/or removing warts, corns and calluses that overcomes the above problems.

SUMMARY OF THE INVENTION

The present invention has the advantage of providing a corn/callus/wart remover medicated plaster, which utilizes polymeric materials other than natural rubber, which might cause undesirable allergic reactions in some individuals.

Another advantage of the present invention is that it provides a medicated plaster disk which significantly reduces "creep" or "cold flow" from the disk upon standing, storage or use. Such creep or cold flow can cause the plaster component of the disk to migrate out from under the plaster substance and slide or smear onto both target non-target areas, such as the packaging, socks, foot or skin surface, hosiery, shoes and the like.

Another advantage of the present invention is that it provides a medicated plaster, which has sufficient or improved tack or adhesive properties for adhering securely to the site of application on the skin surface.

Another advantage of the present invention is that it provides a medicated plaster, which is efficacious and can release the active ingredient into the skin at a sufficient rate and/or quantity to treat or remove warts, corns and calluses.

Another advantage of the present invention is that it provides a medicated plaster, which has adequate shelf-life stability with respect to the content of the active ingredient at the expiry date assigned to the product.

Another advantage of the present invention is that it provided for a medicated product whose plaster component has improved and more uniform product consistency compared to previous devices.

Another advantage of the present invention is that it provides a medicated device, which is simpler to manufacture, compared to devices, which utilize natural rubbers.

DETAILED DESCRIPTION OF THE INVENTION

The present invention is directed to medicated plaster preparations comprising salicylic acid or a pharmaceutically acceptable salt or ester thereof. The present invention includes medicated plaster preparations comprising a synthetic rubber; a reinforcing agent based on silica or random styrene-butadiene, copolymer; a tackifier; salicylic acid or a pharmaceutically acceptable salt or ester thereof, and optionally other ingredients.

The term "medicated plaster" refers to a combination of salicylic acid or a salt, ester or mixture intimately dispersed in a plaster preparation.

The term "plaster" refers to any non-liquid vehicle, which can be applied to the skin or nail and which can hold the salicylic acid against the skin or nail surface. Suitable plaster vehicles include, but are not limited to, plasters or preformed films based upon rubbers, acrylics, polyvinylalkylethers, gels or impregnated microporous membranes. Alternatively, the plaster could be combined with or formed into shape of an artificial or fake nail to improve cosmetic appearance.

Preferably, the plaster preparation is self-adhesive, i.e. self-adhering to the nail or skin, although any suitable means such as a bandage could be used to hold the plaster against the nail or skin surface.

The term "rubber" or "synthetic rubber" refers to any of a number of synthetic (i.e. man-made) high molecular weight homopolymers (e.g., weight average nuclear weight of 50,000 Daltons or higher) and/or random synthetic copolymers having unique properties of deformation (elongation or yield under stress). Thus, the present invention does not include the class of rubbers known as "natural rubbers" whose properties from batch to batch may be highly variable and whose use may give rise to allergic reactions in certain individuals. Preferably the synthetic rubber has a low glass transition temperature such as from −10° C. to about −100° C. Representative synthetic rubbers can include nitrile butadiene rubbers (NBR), polyisoprene rubbers, polybutadiene rubbers (PBD), and styrene-butadiene rubbers (SBR). Preferably the synthetic rubber is cis-1,4polyisoprene, commercially available, for example, as Natsyn 2200 or Natsyn 2205, available from the Goodyear Tire and Rubber Company, Akron, Ohio. The amount of synthetic rubber in the plaster formulation can range from about 15 to about 50% by weight of the plaster formulation, more preferably from about 20 to about 40% by weight, most preferably from about 25 to about 35% by weight.

The plaster preparations can be reinforced with a suitable reinforcing agent such as silica-based compositions such as silica, zirconium silicate or silica aerogels. Preferably the reinforcing agent is a silica-based composition, including any of the following silicas: silazane treated silica, precipitated silica, fumed silica, mined silica or mixtures of any of the above, as well as various reinforcing silica fillers taught in U.S. Pat. No. 3,635,743. More preferably, the reinforcing filler is a precipitated amorphous silica (silicon dioxide), such as that found in the Hi Sil 2000 Series, available from PPG Industries, Chemical Division, Pittsburgh, Pa. The surface area of the silica-based reinforcing agent can range from about 80 to about 400 square meters/gram ($m^2/g$), preferably from about 200 to about 400 $m^2/g$. Where the reinforcing agent is silica-based, the amount of reinforcing agent in the plaster preparation can range from about 2 to about 20% by weight of the plaster preparation, more preferably from about 5 to about 15% by weight, most preferably from about 6 to about 12% by weight. Alternatively, the reinforcing agent can be a styrene-butadiene rubber or copolymer (SBR), preferably a random styrene-butadiene rubber such as Plioflex 1028 M85-017 and Plioflex 1027 available from the Goodyear Tire and Rubber Company. Where the reinforcing agent is a styrene-butadiene rubber, the amounts of the reinforcing agent can range from about 5 to about 40% by weight of plaster preparation, preferably from about 10 to about 30% by weight of the plaster preparation, more preferably from about 12 to about 20% by weight.

A tackifier is a substance, which enhances the tack or adhesive properties of the plaster preparation. Suitable tackifiers include rosin acid derivatives such as Pentalyn H from the Hercules Corporation, terpene based derivatives and synthetic C-5 tackifiers based on synthetic derivatives of petroleum stream fractions such as Escorez 2520 and Escorez 1310 from the Exxon Corporation or synthetic polyterpene resins such as Wingtack 10 from the Goodyear Tire and Rubber Company. The amount of tackifier in the plaster preparation can range from about 2 to about 20% by weight of the plaster preparation, preferably from about 5 to about 15%, more preferably from about 6 to about 12% by weight.

Salicylic acid, salts or esters thereof can be employed as the active ingredient in the plaster preparation. Suitable salts include the sodium, potassium, calcium, lithium or magnesium salts thereof. Suitable esters include the C-1 to C-4 esters thereof, such as methyl salicylate. Other esters include salsalate (salicylsalicylic acid), the salicylate ester of salicylic acid. Most preferably the acid form is employed as the active ingredient. Salicylic acid is also known as 2-hydroxybenzoic acid. Also preferred is that Salicylic Acid Powder USP grade is employed. The amount of salicylic acid in the plaster preparation can range from about 12 to about 60% by weight of the plaster formulation, preferably from about 20 to about 45% by weight, more preferably from about 36 to about 44% by weight. The salicylic acid can be admixed with mineral oil as a processing aid.

A processing aid or lubricant, such as mineral oil, may be used in the preparation of the plaster preparation. Mineral oil refers to an oil derived from a liquid petroleum derivative. Preferably, the mineral oil is USP grade, extra heavy. Also preferred is that the mineral oil has a viscosity in the range of about 360 to about 390 SUS. The amount of mineral oil in the plaster preparation can range from about 1 to about 10% by weight of the plaster preparation, preferably from about 2 to about 8% by weight, more preferably from about 4 to about 6% by weight.

A pigment may optionally be employed in the plaster preparation to provide a darker coloration, such as a brown or reddish brown color, to the plaster preparation. Preferably the pigment can be an iron oxide pigment or a blend of iron oxides and talc, such as Umber Iron Oxide 19850, available from the Warner-Jenkinson Company, A Division of Warner-Jenkinson Co., Inc., 107 Wade Street, P. O. Box 705, South Plainfield, N.J. 07080. The amount of the pigment employed in the plaster preparation can range from about 0% (i.e. none) to about 2% by weight of the plaster preparation, preferably from about 0.25 to about 1%, more preferably from about 0.4 to about 0.6% by weight.

An antioxidant may optionally be employed in the plaster preparation to retard deterioration of the plaster formulation by oxidation. Suitable antioxidants include 4-(4,6-bis (octylthio)-5-triazin-2-yl)amino)-2,6-di-tert-butylphenol, also known as Irganox 565, and 2-methyl4,6-bis((octylthio) methyl)phenol (expoxidized triglyceride), also known as Irganox 1520 LR, available from the Novartis Corporation, Summit, N.J. The amount of the antioxidant employed in the plaster preparation can range from about 0% (i.e. none) to about 1% by weight of the plaster preparation, more preferably from about 0.05 to about 0.5% by weight.

Optionally, other ingredients can be employed in the topical preparation to assist penetration of salicylic acid into the nail and/or skin. Such agents can include nail softeners and avulsers, such as urea, sulfhydryl agents and sulfur-based reducing agents such as sodium sulfide, nail penetration enhancers, and occluding agents and/or hydrophillic fillers to promote hydration of the nail and/or skin.

Where the medicated device is intended to treat disorders or diseases of the nail (i.e. onychomycosis), other active ingredients can be added, such as antifungal agents including clotrimazole butenafine, SP terbinaFine, miconazole, etc. in amounts up to 20% by weight of the plaster. Also, nail softening agents can also be added to the plaster formulation, such as urea, acetyl cysteine, N-ethylmaleimide, sodium sulfide, thioglycolic acid, etc. in amounts up to 20% by weight of the plaster.

The plaster preparations may be prepared as follows. A powdered blend of the active ingredient(s), the reinforcing agent and mineral oil is prepared in a high intensity powder mixer, ribbon blender or other appropriate mixer. The synthetic rubber is banded on a two-roll rubber mill and the antioxidant (if any) is added to the rolling bank of rubber in the nip between the rolls. The powdered blend is added to the rolling bank of rubber on the mill portion by portion; at the same time, the liquid tackifier is added portionwise to help incorporate the powdered blend into the rubber. As the above ingredients are mixing, the pigment is added to the rubber mix on the mill to form the raw plaster. The raw plaster is allowed to continue to mix on the mill with cutting and folding over plaster into the nip until it is uniformly mixed, as evaluated by consistency and appearance. The raw plaster is then cut on the bias across the roll and removed from the mill for subsequent processing such as calendering and/or die-cutting.

In a more preferred embodiment, the plaster preparation containing salicylic acid and the plaster preparation is attached to a carrier or substrate to form a medicated plater roll or sheet. In the medicated sheet, the carrier can impart occlusive properties and dimensional strength to the plaster preparation. The carrier can also provide dimensional stability to the plaster preparation against disintegration and/or tearing by external forces, such as shear forces exerted on the plaster from normal handling or from rubbing of the skin or nail against the shoe, sock or stocking. The carrier can be selected from a wide range of materials, including those, which can promote occlusion and hydration of the skin and/or nail, such as (but not limited to) a resin-impregnated woven cloth or fabric, flexible polyvinyl chloride film or a flexible polyester film. The carrier can be attached to the plaster preparation by lamination techniques, by coextrusion or by bonding the carrier onto the plaster preparation using adhesives, so that the plaster preparation is adhered to at least one side of the carrier surface. The carrier also serves the function of directing the salicylic acid toward the site of application, thus minimizing its dissipation or dispersion into the shoe or hose materials. The medicated plaster can be formed into any shape suitable for administering the salicylic acid to the skin or nail. Such shapes include but are not limited to disks, squares, rectangles or nail-shaped.

Texture Analyzer creep and Texture Analyzer tack can be measured using a suitable instrument or device such as the TA.XT2i Texture Analyzer of Texture Technologies Corporation, Scarsdale, N.Y., whose website is located at www.texturetechnologies.com. Texture Analyzer Creep is a measure of cold flow of the plaster preparation. The Texture Analyzer Creep can be in the range between about 0 mm and 15 mm, preferably less than 7 mm, more preferably less 10 than 4 mm. The Texture Analyzer Tack, Peak Force is a measure of the tack or adhesive properties of the plaster preparation. The Texture Analyzer Tack, Peak Force can be in the range between about 0 g to about 100 g, preferably greater than 30 g, more preferably greater than 40 g.

The medicated plasters can be topically applied according to a regimen effective to remove warts, corns or calluses of the skin or to treat diseases of the nail. For warts, corns and calluses, the area with the affliction is washed and dried thoroughly. If needed, the medicated plaster is cut to fit over the wart, corn or callus. The medicated plaster is applied with the sticky or tacky side adhering to the skin. Typically, the medicated plaster is covered with an enclosed cushion or pad. After 48 hours the medicated plaster can be removed and replaced with another medicated disk. Optionally, the skin may be soaked in warm water for five minutes or more prior to the treatment to assist in removal of the wart, corn or callus. Typically, the procedure can be repeated every 48 hours as needed for up to 14 days or until the wart, corn or callus is removed.

For treatment of nail diseases, the medicated plaster can be applied to the nail daily or for intermittent intervals, such as for two to three times per week. The duration of treatment can vary greatly, depending upon the degree of severity of the infection, the part of the body where the nail is being treated, the age of the person, the thickness of the nail, the rate of nail growth and the like. Generally, the toenails of a younger person can be expected to receive treatments up to 6 months, whereas the toenails of an older person can be expected to receive treatment up to about one year. These periods reflect the time required for toenails to completely grow out of the toe. Treatment of fingernails can be expected to be faster, since fingernail growth is approximately twice as fast as toenail growth. Effectiveness of the treatment can be evaluated by the subsidence or disappearance of symptoms. Less severe cases where only part of the distal portion of the nail is infected can be expected to require less time for treatment. The medicated device can be topically applied to the entire surface of the nail structure, including the region of the cuticle proximal to the nail fold, which overlies the growth center of the nail known as the matrix.

EXAMPLE 1

A synthetic rubber-based plaster preparation is prepared by blending the following ingredients:

| Ingredient | Amount in Plaster Preparation (%) |
| --- | --- |
| Natsyn 2205 synthetic rubber | 31.72 |
| Hi-Sil 233 silica reinforcer | 8.50 |
| Escorez 2520 tackifier | 11.40 |
| Salicylic acid | 43.00 |
| Mineral Oil | 4.78 |
| Umber Iron Oxide Pigment | 0.50 |
| Irganox 565 Anti-oxidant | 0.10 |
| Total | 100.00 |
| Texture Analyzer Creep | 3.1 mm@23° C./50% RH |
| Texture Analyzer Tack, Peak Force | 49.1 g |

Using a web coating machine with lamination stations, the plaster preparation is coated onto a release liner to form a film (i.e. plaster) containing about 13 milligrams of salicylic acid per square centimeter. The film is laminated onto a carrier and prepared as rollstock. The rollstock is diecut into medicated disks of varying diameters depending on the application (e.g. corn, callus, or wart removal) and with a thickness of about 19 mm.

EXAMPLE 2

A medicated plaster is prepared essentially in accordance with the procedure of Example 1, except that the following synthetic rubber-based plaster preparation is used:

| Ingredient | Amount in Plaster Preparation (%) |
| --- | --- |
| Natsyn 2205 synthetic rubber | 35.99 |
| Hi-Sil 233 silica reinforcer | 0.00 |
| Escorez 2520 tackifier | 16.02 |
| Salicylic acid | 42.74 |
| Mineral Oil | 4.75 |
| Umber Iron Oxide Pigment | 0.50 |
| Irganox 565 Anti-oxidant | 0.00 |
| Total | 100.00 |
| Texture Analyzer Creep | 6.08 mm@23° C./50% RH |
| Texture Analyzer Tack, Peak Force | 73.8 g |

EXAMPLE 3

A medicated disk device is prepared essentially in accordance with the procedure of Example 1, except that the following synthetic rubber-based plaster preparation is used:

| Ingredient | Amount in Plaster Preparation (%) |
| --- | --- |
| Natsyn 2205 synthetic rubber | 36.00 |
| Hi-Sil 233 silica reinforcer | 10.27 |
| Escorez 2520 tackifier | 5.74 |
| Salicylic acid | 42.74 |
| Mineral Oil | 4.75 |
| Umber Iron Oxide Pigment | 0.50 |
| Irganox 565 Anti-oxidant | 0.00 |
| Total | 100.00 |
| Texture Analyzer Creep | 1.41 mm@23° C./50% RH |
| Texture Analyzer Tack, Peak Force | 69.7 g |

EXAMPLE 4

A medicated disk device is prepared essentially in accordance with the procedure of Example 1, except that the following synthetic rubber-based plaster preparation is used:

| Ingredient | Amount in Plaster Preparation (%) |
| --- | --- |
| Natsyn 2205 synthetic rubber | 25.73 |
| Hi-Sil 233 silica reinforcer | 10.29 |
| Escorez 2520 tackifier | 15.99 |
| Salicylic acid | 42.75 |
| Mineral Oil | 4.75 |
| Umber Iron Oxide Pigment | 0.50 |
| Irganox 565 Anti-oxidant | 0.00 |
| Total | 100.00 |
| Texture Analyzer Creep | 2.85 mm@23° C./50% RH |
| Texture Analyzer Tack, Peak Force | 64.8 g |

EXAMPLE 5

A medicated disk device is prepared essentially in accordance with the procedure of Example 1, except that a random styrene-butadiene rubber-based reinforcing agent is used in place of the silica-based reinforcing agent:

| Ingredient | Amount in Plaster Preparation (%) |
|---|---|
| Natsyn 2205 synthetic rubber | 28.46 |
| Random Styrene-butadiene rubber | 18.07 |
| Escorez 2520 tackifier | 5.21 |
| Salicylic acid | 42.94 |
| Mineral Oil | 4.77 |
| Umber Iron Oxide Pigment | 0.55 |
| Irganox 565 Anti-oxidant | 0.00 |
| Total | 100.00 |
| Texture Analyzer Creep | 3.22 mm@23° C./50% RH |
| Texture Analyzer Tack, Peak Force | 16.4 g |

EXAMPLE 6

A medicated disk device is prepared essentially in accordance with the procedure of Example 1, except that a styrene-butadiene rubber-based reinforcing agent is used in place of the silica-based reinforcing agent:

| Ingredient | Amount in Plaster Preparation (%) |
|---|---|
| Natsyn 2205 synthetic rubber | 15.50 |
| Random Styrene-butadiene rubber | 18.12 |
| Escorez 2520 tackifier | 18.06 |
| Salicylic acid | 43.04 |
| Mineral Oil | 4.78 |
| Umber Iron Oxide Pigment | 0.50 |
| Irganox 565 Anti-oxidant | 0.00 |
| Total | 100.00 |
| Texture Analyzer Creep | 6.77 mm@23° C./50% RH |
| Texture Analyzer Tack, Peak Force | 36.5 g |

EXAMPLE 7

A medicated disk device is prepared essentially in accordance with the procedure of Example 1, except that a styrene-butadiene rubber-based reinforcing agent is used in place of the silica-based reinforcing agent:

| Ingredient | Amount in Plaster Preparation (%) |
|---|---|
| Natsyn 2205 synthetic rubber | 28.48 |
| Random Styrene-butadiene rubber | 5.19 |
| Escorez 2520 tackifier | 18.17 |
| Salicylic acid | 42.91 |
| Mineral Oil | 4.77 |
| Umber Iron Oxide Pigment | 0.49 |
| Irganox 565 Anti-oxidant | 0.00 |
| Total | 100.00 |
| Texture Analyzer Creep | 7.25 mm@23° C./50% RH |
| Texture Analyzer Tack, Peak Force | 70.4 g |

EXAMPLE 8

The amount of salicylic acid released can be measured on medicated plaster disks by placing disks into vials with distilled water, placing the vials in a temperature-controlled shaker bath (32 degrees C.), and analyzing aliquots from the vials for salicylic acid by liquid chromatographic techniques at selected time points. The amounts of "reinforcing agent" (eg precipitated silica) and tackifier in the plaster formulation, in addition to controlling the balance of "cold flow" and "tack" (as described in the above Examples), can also be used to control the salicylic acid release characteristics. The following Table illustrates the effects of varying tackifier and "reinforcer" level:

| Plaster No. | % HiSil 233 Reinforcer | % Escorez 2520 Tackifier | % S.A. Release 8-- | 24-- | 48 Hour |
|---|---|---|---|---|---|
| 1 | 10.3 | 15.5 | 36.8 | 58.5 | 77.0 |
| 2 | 8.5 | 11.4 | 33.6 | 58.8 | 76.8 |
| 3* | 6.7 | 11.9 | 27.8 | 47.8 | 65.8 |
| 4 | 0.0 | 5.2 | 22.8 | 40.4 | 58.7 |
| 5 | 0.0 | 25.9 | 16.4 | 29.4 | 41.8 |

Plaster No. 3 of this Example is the medicated plaster is described in Example 4 above. The "cold flow" and "tack" values for this medicated plaster meet the criteria for both properties previously described above.

What is claimed is:

1. A plaster preparation comprising:
   a) a synthetic rubber;
   b) a reinforcing agent based on silica or random styrene-butadiene copolymer;
   c) a tackifier; and
   d) salicylic acid or a pharmaceutically acceptable salt or ester thereof.

2. The plaster preparation of claim 1 wherein said a) synthetic rubber is made of high molecular weight homopolymers and/or random synthetic copolymers.

3. The plaster preparation of claim 1 wherein said a) synthetic rubber is nitrile butadiene rubber, polyisoprene rubber, polybutadiene rubber or styrene-butadiene rubbers.

4. The plaster preparation of claim 1 wherein the synthetic rubber is cis-1,4-polyisoprene.

5. The plaster preparation of claim 1 wherein the reinforcing agent is based on silica.

6. The plaster preparation of claim 1 wherein the reinforcing agent is a precipated silica.

7. The plaster preparation of claim 1 wherein the reinforcing agent is a precipitated amorphous silica.

8. The plaster preparation of claim 1 wherein the reinforcing agent is based on random styrene-butadiene rubber copolymer.

9. The plaster preparation of claim 1 wherein the tackifier is a C-5 tackifier.

10. The plaster preparation of claim 1 wherein the salicylic acid is in the acid form.

11. A medicated device comprising:
   i) a plaster preparation comprising:
      a) a synthetic rubber;
      b) a reinforcing agent based on silica or styrene-butadiene;
      c) a tackifier; and
      d) salicylic acid or a phannaceutically acceptable salt or ester thereof, and
   ii) a carrier to which the plaster preparation is adhered.

12. The medicated device of claim 11 wherein said a) synthetic rubber is made of high molecular weight homopolymers and/or random synthetic copolymers.

13. The medicated device of claim 11 wherein said a) synthetic rubber is nitrile butadiene rubber, polyisoprene rubber, polybutadiene rubber or styrene-butadiene rubber.

14. The medicated device of claim 11 wherein the synthethic rubber is cis-1,4-polyisoprene.

15. The medicated device of claim 11 wherein the reinforcing agent is based on silica.

16. The medicated device of claim 11 wherein the reinforcing agent is a precipated silica.

17. The medicated device of claim 11 wherein the reinforcing agent is a precipitated amorphous silica.

18. The medicated device of claim 11 wherein the reinforcing agent is based on random styrene-butadiene rubber copolymer.

19. The medicated device of claim 11 wherein the tackifier is a C-5 tackifier.

20. The medicated device of claim 11 wherein the salicylic acid is in the acid form.

21. A method for treating wart, corn, calluses or diseases of the nail by topically administering to the wart, corn, callus or nail the plaster preparation of claim 1.

* * * * *